US006281387B1

(12) United States Patent
Bhasin et al.

(10) Patent No.: US 6,281,387 B1
(45) Date of Patent: Aug. 28, 2001

(54) PROCESS AND CATALYST FOR SYNTHESIZING ALIPHATIC, CYCLIC AND AROMATIC ALKANOLAMINES AND ALKYLENEAMINES

(75) Inventors: Madan Mohan Bhasin, Charleston; Stephen Wayne King, Scott Depot, both of WV (US)

(73) Assignee: Union Carbide Chemicals & Plastics Technology Corporation, Danbury, CT (US)

(*) Notice: Subject to any disclaimer, the term of this patent is extended or adjusted under 35 U.S.C. 154(b) by 0 days.

(21) Appl. No.: 09/430,634

(22) Filed: Oct. 29, 1999

(51) Int. Cl.$^7$ .................................................. C07C 209/02
(52) U.S. Cl. ......................... 564/469; 564/479; 564/480; 564/485
(58) Field of Search .................................. 564/469, 479, 564/480, 485

(56) References Cited

U.S. PATENT DOCUMENTS 4,307,250   12/1981   Peterson et al. ..................... 564/445

OTHER PUBLICATIONS

Sharpless, K.B. et al., "Osmium–Catalyzed Vicinal Oxyamination of Olefins by Chloramine–T", *J. Org. Chem.*, vol. 41, No. 1, 1976, pp. 177–179.

Contractor, R.M., et al., "Butane Oxidation to Maleic Anhydride in a Recirculating Solids Reactor", *Catalysis* 1987, pp. 645–653.

Sharpless, K. B. et al., "A New Reaction, Stereospecific Vicinal Oxyamination of Olefins by Alkyl Imido Osmium Compounds", *Journal of the American Chemical Society*, 97:8, Apr. 16, 1975, pp. 2305–2307.

Keller, G.E. et al., "Synthesis of Ethylene via Oxidative Coupling of Methane", *Journal of Catalysis* 73, 9–19 (1982).

Li, G. et al., "Catalytic Asymmetric Aminohydroxylation (AA) of Olefins", *Angew. Chem. Int. Ed. Engl.* 1996, 35, No. 4, pp. 451–454.

Moro–Oka, Y. et al., "Multicomponent Bismuth Molybdate Catalyst: A Highly Functionalized Catalyst System for the Selective Oxidation of Olefin", *Advances in Catalysis*, vol. 40, pp. 233–273.

Contractor, R.M. et al., "Butane Oxidation to Maleic Anhydride Over Vanadian Phosphate Catalysts", *Catalysis Today*, 1 (1987), pp. 49–58.

Contractor, R. et al., "Butane Oxidation in a Transport Bed Reactor—Redox Characteristics of the Vanadium Phosphorus Oxide Catalyst", *New Developments in Selective Oxidation* 1990, pp. 553–562.

Brazdil, J.F., "Acrylonitrile", *Kirk–Othmer Encyclopedia of Chemical Technology*, 1991, vol. pp. 352–370.

Haruta, Masatake, "Size– and Support–Dependency in the Catalysis of Gold", *Catalysis Today* 36 (1997) 153–166.

Takahashi, N. et al., "Acetonitrile Formation from Ethylene and Ammonia over $Zn^{2+}$ and $Cd^{2+}$ Exchanged Y–zeolites", *Chemistry Letters*, pp. 1323–1324, 1994.

Li, Y. et al., "Ammoxidation of Ethane to Acetonitrile over Metal–Zeolite Catalysts", *Journal of Catalysis* 173, 511–518 (1998), Article No. CA971947.

Li, Y. et al., "Ammoxidation of Ethane to Acetonitrile over Co–Beta Zeolite", *Chem. Commun.*, 1997, pp. 2013–2014.

Takahashi, N. et al., "Catalytic Behavior of $Zn^{2+}$ and $Cd^{2+}$ supported Y–zeolite for Acetonitrile Formation from Ethene and Ammonia", *Applied Catalysis A: General* 164 (1997) 281–289.

Contractor, R.M. et al., "Circulating Fluidized Bed as a Catalytic Reactor", pp. 39–48.

Contractor, R.M. et al., "Attrition Resistant Catalysts for Fluidized Bed Systems", pp. 589–596.

Contractor, R.M. et al., "A New Commercial Scale Process for n–Butane Oxidation to Maleic Anhydride Using a Circulating Fluidized Bed Reactor", *New Developments in Selective Oxidation II*, V. Cortes Corberan and S. Vic Bellon (Editors), 1994, pp. 233–242.

*Primary Examiner*—Johann Richter
*Assistant Examiner*—Brian J. Davis (57) ABSTRACT

The invention provides a process for synthesizing alkanolamines and/or alkyleneamines by reacting either an alkane, an alkene, or both with a source of oxygen and a source of nitrogen and, optionally, additional hydrogen to convert the alkane and/or alkene by selective partial oxidative amination to at least one of the desired end products. The invention further provides a regenerable catalyst for use in synthesizing alkanolamines and/or alkyleneamines by selective partial oxidative amination of alkanes and/or alkenes.

15 Claims, 9 Drawing Sheets

FIG. 1B

Ethylene Based Route to MEA Reactions.

1. $C_2H_4$ (g) + $NH_3$ (g) + 0.5 $O_2$ (g) → $HO\text{-}C_2H_4\text{-}NH_2$ (g)
2. $C_2H_4$ (g) + $NH_3$ (g) + $SrO_2$ (s) → $HO\text{-}C_2H_4\text{-}NH_2$ (g) + $SrO$ (s)
3. $C_2H_4$ (g) + $NH_3$ (g) + 2 $MnO_2$ (s) → $HO\text{-}C_2H_4\text{-}NH_2$ (g) + $Mn_2O_3$ (s)
4. $C_2H_4$ (g) + $NH_3$ (g) + 3 $Mn_2O_3$ (s) → $HO\text{-}C_2H_4\text{-}NH_2$ (g) + 2 $Mn_3O_4$ (s)
5. $C_2H_4$ (g) + $NH_3$ (g) + $V_2O_5$ (s) → $HO\text{-}C_2H_4\text{-}NH_2$ (g) + $V_2O_4$ (s)
6. $C_2H_4$ (g) + $NH_3$ (g) + $MoO_3$ (s) → $HO\text{-}C_2H_4\text{-}NH_2$ (g) + $MoO_2$ (s)
7. $C_2H_4$ (g) + $NH_3$ (g) + $Cu_2O$ (s) → $HO\text{-}C_2H_4\text{-}NH_2$ (g) + 2 Cu (s)
8. $C_2H_4$ (g) + $NH_3$ (g) + $Co_3O_4$ (s) → $HO\text{-}C_2H_4\text{-}NH_2$ (g) + 3 CoO (s)
9. $C_2H_4$ (g) + $NH_3$ (g) + PbO (s) → $HO\text{-}C_2H_4\text{-}NH_2$ (g) + Pb (s)
10. $C_2H_4$ (g) + $NH_3$ (g) + $Mn_3O_4$ (s) → $HO\text{-}C_2H_4\text{-}NH_2$ (g) + 3 MnO (s)
11. $C_2H_4$ (g) + $NH_3$ (g) + 3 $Fe_2O_3$ (s) → $HO\text{-}C_2H_4\text{-}NH_2$ (g) + 2 $Fe_3O_4$ (s)
12. $C_2H_4$ (g) + $NH_3$ (g) + $WO_3$ (s) → $HO\text{-}C_2H_4\text{-}NH_2$ (g) + $WO_2$ (s)
13. $C_2H_4$ (g) + $NH_3$ (g) + $SnO_2$ (s) → $HO\text{-}C_2H_4\text{-}NH_2$ (g) + SnO (s)
14. $C_2H_4$ (g) + $NH_3$ (g) + 0.5 $WO_2$ (s) → $HO\text{-}C_2H_4\text{-}NH_2$ (g) + 0.5 W (s)

FIG. 2A

Ethylene Based Route to EDA

FIG. 2B

Ethylene Based Route to EDA Reactions.

1. $C_2H_4$ (g) + 2 $NH_3$ (g) + 0.5 $O_2$ (g) → $H_2N$-$C_2H_4$-$NH_2$ (g) + $H_2O$ (g)
2. $C_2H_4$ (g) + 2 $NH_3$ (g) + $SrO_2$ (s) → $H_2N$-$C_2H_4$-$NH_2$ (g) + $H_2O$ (g) + SrO (s)
3. $C_2H_4$ (g) + 2 $NH_3$ (g) + 2 $MnO_2$ (s) → $H_2N$-$C_2H_4$-$NH_2$ (g) + $H_2O$ (g) + $Mn_2O_3$ (s)
4. $C_2H_4$ (g) + 2 $NH_3$ (g) + 3 $Mn_2O_3$ (s) → $H_2N$-$C_2H_4$-$NH_2$ (g) + $H_2O$ (g) + 2 $Mn_3O_4$ (s)
5. $C_2H_4$ (g) + 2 $NH_3$ (g) + $V_2O_5$ (s) → $H_2N$-$C_2H_4$-$NH_2$ (g) + $H_2O$ (g) + $V_2O_4$ (s)
6. $C_2H_4$ (g) + 2 $NH_3$ (g) + $MoO_3$ (s) → $H_2N$-$C_2H_4$-$NH_2$ (g) + $H_2O$ (g) + $MoO_2$ (s)
7. $C_2H_4$ (g) + 2 $NH_3$ (g) + $Cu_2O$ (s) → $H_2N$-$C_2H_4$-$NH_2$ (g) + $H_2O$ (g) + 2 Cu (s)
8. $C_2H_4$ (g) + 2 $NH_3$ (g) + $Co_3O_4$ (s) → $H_2N$-$C_2H_4$-$NH_2$ (g) + $H_2O$ (g) + 3 CoO (s)
9. $C_2H_4$ (g) + 2 $NH_3$ (g) + PbO (s) → $H_2N$-$C_2H_4$-$NH_2$ (g) + $H_2O$ (g) + Pb (s)
10. $C_2H_4$ (g) + 2 $NH_3$ (g) + $Mn_3O_4$ (s) → $H_2N$-$C_2H_4$-$NH_2$ (g) + $H_2O$ (g) + 3 MnO (s)
11. $C_2H_4$ (g) + 2 $NH_3$ (g) + 3 $Fe_2O_3$ (s) → $H_2N$-$C_2H_4$-$NH_2$ (g) + $H_2O$ (g) + 2 $Fe_3O_4$ (s)
12. $C_2H_4$ (g) + 2 $NH_3$ (g) + $WO_3$ (s) → $H_2N$-$C_2H_4$-$NH_2$ (g) + $H_2O$ (g) + $WO_2$ (s)
13. $C_2H_4$ (g) + 2 $NH_3$ (g) + $SnO_2$ (s) → $H_2N$-$C_2H_4$-$NH_2$ (g) + $H_2O$ (g) + SnO (s)
14. $C_2H_4$ (g) + 2 $NH_3$ (g) + 0.5 $WO_2$ (s) → $H_2N$-$C_2H_4$-$NH_2$ (g) + $H_2O$ (g) + 0.5 W (s)

FIG. 3B

Ethane Based Route to MEA Reactions.

1. $C_2H_6(g) + NH_3(g) + O_2(g) \longrightarrow HO\text{-}C_2H_4\text{-}NH_2(g) + H_2O(g)$
2. $C_2H_6(g) + NH_3(g) + 2\ SrO_2(s) \longrightarrow HO\text{-}C_2H_4\text{-}NH_2(g) + H_2O(g) + 2\ SrO(s)$
3. $C_2H_6(g) + NH_3(g) + 4\ MnO_2(s) \longrightarrow HO\text{-}C_2H_4\text{-}NH_2(g) + H_2O(g) + 2\ Mn_2O_3(s)$
4. $C_2H_6(g) + NH_3(g) + 6\ Mn_2O_3(s) \longrightarrow HO\text{-}C_2H_4\text{-}NH_2(g) + H_2O(g) + 4\ Mn_3O_4(s)$
5. $C_2H_6(g) + NH_3(g) + 2\ V_2O_5(s) \longrightarrow HO\text{-}C_2H_4\text{-}NH_2(g) + H_2O(g) + 2\ V_2O_4(s)$
6. $C_2H_6(g) + NH_3(g) + 2\ MoO_3(s) \longrightarrow HO\text{-}C_2H_4\text{-}NH_2(g) + H_2O(g) + 2\ MoO_2(s)$
7. $C_2H_6(g) + NH_3(g) + 2\ Cu_2O(s) \longrightarrow HO\text{-}C_2H_4\text{-}NH_2(g) + H_2O(g) + 4\ Cu(s)$
8. $C_2H_6(g) + NH_3(g) + 2\ Co_3O_4(s) \longrightarrow HO\text{-}C_2H_4\text{-}NH_2(g) + H_2O(g) + 6\ CoO(s)$
9. $C_2H_6(g) + NH_3(g) + 2\ PbO(s) \longrightarrow HO\text{-}C_2H_4\text{-}NH_2(g) + H_2O(g) + 2\ Pb(s)$
10. $C_2H_6(g) + NH_3(g) + 2\ Mn_3O_4(s) \longrightarrow HO\text{-}C_2H_4\text{-}NH_2(g) + H_2O(g) + 6\ MnO(s)$
11. $C_2H_6(g) + NH_3(g) + 6\ Fe_2O_3(s) \longrightarrow HO\text{-}C_2H_4\text{-}NH_2(g) + H_2O(g) + 4\ Fe_3O_4(s)$
12. $C_2H_6(g) + NH_3(g) + 2\ WO_3(s) \longrightarrow HO\text{-}C_2H_4\text{-}NH_2(g) + H_2O(g) + 2\ WO_2(s)$
13. $C_2H_6(g) + NH_3(g) + 2\ SnO_2(s) \longrightarrow HO\text{-}C_2H_4\text{-}NH_2(g) + H_2O(g) + 2\ SnO(s)$
14. $C_2H_6(g) + NH_3(g) + WO_2(s) \longrightarrow HO\text{-}C_2H_4\text{-}NH_2(g) + H_2O(g) + W(s)$

FIG. 4B

Ethane Based Route to EDA Reactions.

1. $C_2H_6$ (g) + 2 $NH_3$ (g) + $O_2$ (g) → $H_2N$-$C_2H_4$-$NH_2$ (g) + 2 $H_2O$ (g)
2. $C_2H_6$ (g) + 2 $NH_3$ (g) + 2 $SrO_2$ (s) → $H_2N$-$C_2H_4$-$NH_2$ (g) + 2 $H_2O$ (g) + 2 SrO (s)
3. $C_2H_6$ (g) + 2 $NH_3$ (g) + 4 $MnO_2$ (s) → $H_2N$-$C_2H_4$-$NH_2$ (g) + 2 $H_2O$ (g) + 2 $Mn_2O_3$ (s)
4. $C_2H_6$ (g) + 2 $NH_3$ (g) + 6 $Mn_2O_3$ (s) → $H_2N$-$C_2H_4$-$NH_2$ (g) + 2 $H_2O$ (g) + 4 $Mn_3O_4$ (s)
5. $C_2H_6$ (g) + 2 $NH_3$ (g) + 2 $V_2O_5$ (s) → $H_2N$-$C_2H_4$-$NH_2$ (g) + 2 $H_2O$ (g) + 2 $V_2O_4$ (s)
6. $C_2H_6$ (g) + 2 $NH_3$ (g) + 2 $MoO_3$ (s) → $H_2N$-$C_2H_4$-$NH_2$ (g) + 2 $H_2O$ (g) + 2 $MoO_2$ (s)
7. $C_2H_6$ (g) + 2 $NH_3$ (g) + 2 $Cu_2O$ (s) → $H_2N$-$C_2H_4$-$NH_2$ (g) + 2 $H_2O$ (g) + 4 Cu (s)
8. $C_2H_6$ (g) + 2 $NH_3$ (g) + 2 $Co_3O_4$ (s) → $H_2N$-$C_2H_4$-$NH_2$ (g) + 2 $H_2O$ (g) + 6 CoO (s)
9. $C_2H_6$ (g) + 2 $NH_3$ (g) + 2 PbO (s) → $H_2N$-$C_2H_4$-$NH_2$ (g) + 2 $H_2O$ (g) + 2 Pb (s)
10. $C_2H_6$ (g) + 2 $NH_3$ (g) + 2 $Mn_3O_4$ (s) → $H_2N$-$C_2H_4$-$NH_2$ (g) + 2 $H_2O$ (g) + 6 MnO (s)
11. $C_2H_6$ (g) + 2 $NH_3$ (g) + 6 $Fe_2O_3$ (s) → $H_2N$-$C_2H_4$-$NH_2$ (g) + 2 $H_2O$ (g) + 4 $Fe_3O_4$ (s)
12. $C_2H_6$ (g) + 2 $NH_3$ (g) + 2 $WO_3$ (s) → $H_2N$-$C_2H_4$-$NH_2$ (g) + 2 $H_2O$ (g) + 2 $WO_2$ (s)
13. $C_2H_6$ (g) + 2 $NH_3$ (g) + 2 $SnO_2$ (s) → $H_2N$-$C_2H_4$-$NH_2$ (g) + 2 $H_2O$ (g) + 2 SnO (s)
14. $C_2H_6$ (g) + 2 $NH_3$ (g) + $WO_2$ (s) → $H_2N$-$C_2H_4$-$NH_2$ (g) + 2 $H_2O$ (g) + W (s)

FIG. 5

PROCESS AND CATALYST FOR SYNTHESIZING ALIPHATIC, CYCLIC AND AROMATIC ALKANOLAMINES AND ALKYLENEAMINES

FIELD OF THE INVENTION

The present invention relates to the synthesis of aliphatic, cyclic and aromatic alkanolamines and alkyleneamines (collectively referred to throughout the specification including the claims as "alkanolamines and alkyleneamines") from alkanes and/or alkenes. More particularly, the present invention provides a process for synthesizing alkanolamines and alkyleneamines by selective partial oxidative amination of alkanes and/or alkenes. The invention further provides a regenerable catalyst which provides a favorable free energy for the selective partial oxidative amination reaction.

BACKGROUND OF THE INVENTION

Alkanolamines and alkyleneamines are currently manufactured using alkylene oxides and ammonia as the key starting raw materials. For example, monoethanolamine, di- and tri-ethanolamine and ethylenediamine are currently manufactured using ethylene oxide and ammonia as the starting raw materials. The manufacture of monoethanolamine requires high ammonia to ethylene oxide ratios in order to increase the selectivity to monoethanolamine. It is then necessary to refine and recycle the excess ammonia which significantly increases the cost of monoethanolamine production. Once monoethanolamine is formed, it is treated with ammonia by a reductive amination process to produce ethylenediamine and other higher acyclic and cyclic polyethyleneamines. Again, high ammonia ratios are employed to improve the selectivity to the desired end product, typically, ethylenediamine.

Ethylene oxide is a relatively expensive compound, and the high cost of this material also unfavorably impacts the economics of monoethanolamine and ethylenediamine manufacture. In the case of monoethanolamine, for example, the raw materials may account for at least 70% of the total monoethanolamine cost.

Another commercial process utilizes ethylene dichloride and ammonia for the synthesis of ethylenediamine and other higher homologs. This process is energy intensive and requires expensive refining equipment. Furthermore, the resultant hydrochloride salts of ammonia and the polyethyleneamines must undergo neutralization with caustic (usually sodium hydroxide) to give the free amine product. Separation of the polyethyleneamines and the salt is difficult, and the byproduct salt must be disposed of which further increases the cost of the process.

A process which could produce alkanolamines and alkyleneamines from alkanes and/or alkenes as the starting hydrocarbon raw materials would provide a desirable advantage over the current prior art. In the case of monoethanolamine and ethylenediamine, for example, using ethane and/or ethylene as the starting raw material(s) would provide significantly improved variable costs compared to ethylene oxide and ethylene dichloride. It would also avoid the need to handle ethylene oxide—a highly reactive chemical.

The partial oxidative amination of alkanes and alkenes provides a thermodynamically favorable route to alkanolamines and alkyleneamines, as demonstrated further below. The primary concern with respect to the partial oxidative amination of alkanes and alkenes is selectivity, i.e., the formation of desirable alkanolamines and alkyleneamines rather than the complete conversion of the starting materials to $CO_2$ and water. In addition, preventing or limiting the oxidation of ammonia and other nitrogen sources to $NO_x$ type species and limiting $NO_x$/hydrocarbon reactions are other significant concerns.

A process that effectively addresses these concerns would achieve a novel and practicable means of producing alkanolamines and alkyleneamines. Such an approach would also provide clear economic advantages over the present method of synthesizing these materials from ethylene oxide or ethylene dichloride.

SUMMARY OF THE INVENTION

The present invention meets these objectives by providing, in one aspect, a process for producing alkanolamines and/or alkyleneamines by reacting at least one of an alkane and an alkene with a source of oxygen and a source of nitrogen and, optionally, additional hydrogen to convert the alkane and/or alkene by partial oxidative amination to at least one of the desired end products.

Any source of nitrogen suitable for carrying out the reaction may be utilized, such as ammonia, hydrazine, amines, nitrous oxide in the presence of a reducing gas such as $H_2$, hydrocarbon, etc., and other nitrogen-containing compounds. In the case of monoalkanolamines and alkyleneamines, ammonia is preferred.

The necessary oxygen may be obtained from any suitable source, including without limitation, oxygen, ozone, oxides of nitrogen, water, and alcohols. Preferably, oxygen is used to carry out the reaction. The $O_2$ may be fed at any concentration by mixing with $N_2$, He, or other inert gases. A convenient and safe source of oxygen is air. The required oxygen may also be provided by a suitable metal oxide catalyst or by the reaction of a metal oxide catalyst with $N_2O$, $NO_x$ or sulfur oxides which may be generated in situ or supplied to the reaction system indirectly. In a preferred embodiment of the invention, the oxygen is supplied by one or more reducible metal oxide catalysts that are regenerated by exposure to air, $O_2$, other oxygen containing gases, or other suitable oxygen sources.

Sufficient hydrogen for the reaction is typically provided by the ammonia or amine utilized as the nitrogen source, by the alkane and/or alkene raw materials, or by hydroxyl groups present on the surface of the catalyst. However, in the event these sources do not contain sufficient hydrogen, an additional source of hydrogen may be directly or indirectly provided, for example, $H_2$ gas. The necessary hydrogen may also be provided by one or more hydrogenation/dehydrogenation metal catalysts.

In a second aspect, the invention relates to a metal or metal oxide catalyst which provides a favorable standard free energy for the partial oxidative amination reaction.

Reducible metal oxide catalysts have been found to be particularly suitable for synthesizing alkanolamines and alkaneneamines by partial oxidative amination. These types of metal oxides (referred to herein as "red-ox" catalysts) allow for the ready accessibility of lattice oxygen to promote the oxidation of the feed materials, which results in a corresponding reduction of the metal oxide. This is followed by re-oxidation of the catalyst by another oxygen source, such as $O_2$ or an oxygen-containing gas. Examples of effective red-ox catalysts include, but are not limited to, the oxides of cerium, iron, copper, nickel, lead, cadmium, molybdenum, vanadium, bismuth, manganese, barium, cobalt, strontium, tungsten, samarium, osmium, rhenium, rare earth elements, and mixtures of these oxides.

Those metals which are generally known as hydrogenation/dehydrogenation metals are also effective for carrying out the reaction, either alone or in combination with above-mentioned metal oxide catalysts. As explained in more detail below, it is believed that these catalysts generate highly reactive hydroperoxo and/or peroxo species from $O_2$ and $H_2$ and provide the oxygen and hydrogen necessary for the oxidative amination reaction. These catalysts include but are not limited to nickel, palladium, platinum, cobalt, rhodium, iridium, iron, ruthenium, copper, zinc, gold, silver and mixtures of these metals.

Typically, both the red-ox and hydrogenation/ dehydrogenation catalysts are supported on suitable carriers such as cerias, titanias, zirconias, silicas, aluminas, -alumina, silicon carbide, aluminum phosphate molecular sieves (AlPO's), high silica molecular sieve zeolites, MCM-type large pore zeolites, mixtures of these carriers, and other catalyst support materials well-known in the art.

DETAILED DESCRIPTION OF THE INVENTION

The present invention will be described in connection with an explanation of the synthesis of monoethanolamine and ethylenediamine from ethane and/or ethylene. However, as will be apparent to those skilled in the art, the invention may be used to synthesize other alkanolamines and alkyleneamines depending on the particular alkanes and/or alkenes selected as the hydrocarbon starting materials and the choice of raw material feeds Three routes to monoethanolamine based on selective partial oxidative amination of ethylene and ethane, respectively, are set forth below:

(1)

(2)

(3)

The reactions may be carried out in gas, liquid, supercritical, or multiphase media. As noted previously, any suitable source of oxygen, nitrogen, and hydrogen may be utilized to convert ethylene and/or ethane to monoethanolamine. However, when the reactions are carried out in the vapor phase, oxygen and ammonia are the preferred forms of these reactants. As to the hydrocarbon raw materials, it should also be understood that the use of ethylene and ethane are not mutually exclusive, and that a mixture of these reactants may be utilized in the synthesis of monoethanolamine.

The reactions may be carried out over a broad range of temperatures and pressures. Generally, however, conditions of relatively low temperature and relatively high pressure are preferred. Lower temperatures tend to enhance selectivity and reduce or eliminate the formation of undesirable $NO_x$ by-products. Higher pressures generally increase the rate at which the desired end products are formed. Typically, the synthesis is carried out at temperatures ranging from about 25° C. to about 500° C. and at pressures ranging from about 1 atmosphere to about 200 atmospheres.

While not intending to be limited to a particular theory or mechanistic pathway, the partial oxidative amination represented in reaction (1) and (2) proceeds, as presently understood, by the formation of one or both of the following intermediates:

Epoxide Intermediate     Di-Oxygenated Intermediate

In the most preferred embodiment of the invention, reactions (1) and (2) proceed over a reducible and regenerable metal oxide red-ox catalyst. Generally, metal oxides suitable for use in the invention are those metal oxides that are reduced by reaction with a hydrocarbon moiety to a lower oxidative state, such that the metal oxide provides a lower standard free energy for the partial oxidative amination reaction, in this particular case the reaction to produce monoethanolamine. Oxygen from the feed material then re-oxidizes the metal oxide. For the synthesis of monoethanolamine from ethylene and ethane, respectively, exemplary reactions are shown as follows:

(4)

(5)

For other metal oxides, similar red-ox reactions can be depicted as shown above by balancing the appropriate valences and coefficients for the particular metal oxide selected.

It is believed that the necessary oxygen is provided by these catalysts as oxygen which moves from the lattice to the surface (perhaps as $O^{-2}$, $O^-$, or $O_{2-}$ surface species). One possibility that may account for the high activity of these catalysts is that the metal oxides have point defects, step defects, other types of defects or disorders, or cation vacancies within the lattice which provides for the ready accessibility of oxygen. Whatever the basis for their highly active nature, a number of metal oxides are particularly suitable for carrying out the selective partial oxidative amination of alkanes and alkenes including NiO, PbO, CdO, $MoO_3$, $V_2O_4$, $V_2O_5$, BiO, $Bi_2O_3$, CuO, $Cu_2O$, $MnO_2$, $Mn_2O_3$, $Mn_3O_4$ $BaO2$, $Co_3O_4$, $SrO_2$, $WO_2$, $WO_3$, $SnO_2$, $CeO_2$, $OsO_4$, $Re_2O_7$, $Fe_2O_3$, $Fe_3O_4$, rare earth oxides, and mixtures of these metal oxides.

The partial oxidative amination represented in reaction (3) is believed to proceed by the formation of hydroperoxo and peroxo intermediates having the following structure:

hydroperoxo species   peroxo species

These intermediates are formed by reaction of a hydrogenation/dehydrogenation metal catalyst with $O_2$ and then by reaction with $H_2$. The oxygen adsorbed on the catalyst, either as the hydroperoxo or peroxo intermediate, is capable of adding to an olefin which has been added either as a feed material, or generated in situ by oxidation of an alkane or alkene. The intermediate generated from reaction of the oxygen with the olefin is an epoxide. The epoxide then reacts with the nitrogen compound to give the end product. For example, a feed of ethylene and/or ethane with ammonia would produce ethylene oxide as an intermediate which would react with the ammonia to produce monoethanolamine. Monoethanolamine can also react with the ethylene oxide to give diethanolamine as a product. Typically, reaction conditions are controlled to give the desired end product. Those hydrogenation/dehydrogenation metals that are the most active include, but are not limited to, nickel, palladium, platinum, cobalt, rhodium, iridium, iron, ruthenium, copper, zinc, gold, and silver and mixtures of these metals.

The red-ox and hydrogenation/dehydrogenation catalysts described herein can be prepared by conventional procedures known in the art. For example, the catalyst can be incorporated on preformed carriers or supports (these terms are used interchangeably herein) by impregnating the carrier with a liquid solution comprising a form of the element required to effect reaction. The support shape is generally not narrowly critical; accordingly, the carrier may take the form of, for example, pellets, extruded particles, spheres, rings, monoliths and the like. If more than one metal is to be incorporated the metals may be incorporated simultaneously or sequentially, the sequence of which is not narrowly critical. As noted above, typical supports include cerias, titanias, zirconias, silicas, aluminas, -alumina, silicon carbide, aluminum phosphate molecular sieves (AlPO's), high silica molecular sieve zeolites, MCM-type large pore zeolites, mixtures of these carriers, and other catalyst support materials well-known in the art.

Generally, the metal is in the form of a salt which can be easily dissolved in a liquid solvent for incorporation into the particles or monolith structure of the carrier. Several impregnation steps may be required depending on the amount of metal or metal oxide required and the solubility of the salt of the catalytic compound in the solvent. A drying step is generally employed between each impregnation. This is a well known procedure in the art for incorporating metals and metal oxides onto a solid support material. After all of the impregnation steps are completed, the material is then usually heated at higher temperatures, typically from 100–900° C., to effect at least partial decomposition of the salt to the metal oxide. Alternatively, the metal salt may be heated to 100–900° C. after each impregnation and drying step. The drying and heating steps may be done incrementally at various temperatures over suitable periods of time, or these steps can be ramped up to the desired temperature fairly linearly. If desired, the metal oxide can be reduced to the metal, at least partially, with hydrogen or other reducing gases (e.g. carbon monoxide) using methods well known to one skilled in the art.

Alternatively, some form of the requisite metal can be fused, bonded or compressed into solid pellets or larger structures, or composited with one or more support materials, in association with one or more metal oxides and heated as above. The material may be reduced as alluded to above.

Still further, the catalyst can be provided at the time of preparing the support material. For example, one or more metal oxides may be condensed from their respective hydrolyzable monomers to the desired oxides to form oxide powders which can thereafter be blended and compressed to form pellets and larger structures of the catalyst. The materials are then heated and optionally reduced as alluded to above.

In yet another approach, the metal salt may be precipitated on a preformed carrier using methods described in the art. This procedure offers some advantages for depositing the active metal on the outside of the carrier which may lead to improved selectivity. Some further advantages may be realized by preparing the partial oxidative amination catalyst on zeolite-type materials. For zeolites, known ion-exchange procedures may be employed to incorporate various catalytic metal ions. This allows for shape selectivity and can enhance partial oxidative amination over complete oxidation. The procedures for incorporating metals on zeolites are well known.

The use of supports for the catalysts provides a number of significant advantages. Some of the catalysts are not structurally stable under the reaction conditions when utilized over an extended period of time. In a batch reaction this is not a significant issue. However, when the reaction is effected with the catalyst as part of a fixed bed reactor, in a tubular reactor, or in a fluid bed reactor it is desirable that the catalyst have greater structural stability/integrity for the reaction medium.

Attrition can be a significant problem with an unsupported catalyst particularly if used in a fluidized bed reactor. Improved resistance to attrition of the catalyst can be achieved by providing an attrition resistant coating on the surface of the catalyst. The coating should be resistant to the reactants and products and must be sufficiently porous to permit free passage of the reactants and products through the coating to the catalyst site. Polysilicic acid, zinc oxide, titanium oxide, zirconium oxide, other metal oxides and mixtures of these oxides may be used to provide an outer coating on the catalyst which provides better attrition resistance. The techniques used to provide a protective coating are well known to one skilled in the art.

In one embodiment of the invention, the reducible metal oxide catalyst has a microstructure characterized by a plurality of porous microspheres. An attrition resistant coating is provided on the surface of the microspheres. In this particular example, the coating comprises polysilicic acid. However, as mentioned above the coating may be formed from other inert materials that will also provide attrition resistance, such as zinc oxide, $TiO_2$, $ZrO_2$ and other metal oxides.

Referring now to the synthesis of ethylenediamine, the conversion of ethylene and ethane, respectively, to form ethylenediamine is represented by the following reactions:

$$CH_2=CH_2+\tfrac{1}{2}O_2+2NH_3 \rightarrow H_2NCH_2CH_2NH_2+H_2O \quad (6)$$

$$CH_3-CH_3+O_2+2NH_3 \rightarrow H_2NCH_2CH_2NH_2+2H_2O \quad (7)$$

The following illustrates an optimal reaction for forming ethylenediamine by means of hydroperoxo and/or peroxo intermediates:

$$CH_2=CH_2+\tfrac{1}{2}O_2+H_2+2NH_3 \rightarrow H_2NCH_2CH_2NH_2+H_2O \quad (8)$$

The partial oxidative amination of ethane and/or ethylene to ethylenediamine proceeds under essentially the same reaction conditions and in essentially the same manner as that described above in connection with the synthesis of monoethanolamine. Accordingly, the reactions may be carried out in gas, liquid, supercritical or multiphase media. Various sources of oxygen and nitrogen may be utilized to convert ethylene and ethane to ethylenediamine; however, oxygen gas, preferably mixed with an inert gas, and ammonia are preferred. Either ethylene or ethane may be used as the starting hydrocarbon raw material for the synthesis of ethylenediamine, or, a mixture of these starting materials may be employed. The partial oxidative amination reactions may be carried out over a broad range of temperatures and pressures. Generally, however, the same conditions of relatively low temperature and relatively high pressure discussed above in connection with the synthesis of monoethanolamine are preferred. Thus, the synthesis of ethylenediamine is typically carried out at temperatures ranging from about 25° C. to about 500° C. and at pressures ranging from about 1 atmosphere to about 200 atmospheres.

As in the case of monoethanolamine, the partial oxidative amination of ethane and/or ethylene to produce ethylenediamine is preferably carried out over a reducible metal oxide catalyst which provides the oxygen necessary for the reaction. The metal oxides suitable for synthesizing ethylenediamine are the same catalysts described above in connection with the synthesis of monoethanolamine.

In a preferred embodiment of the invention, the catalyst is continuously regenerated and recycled as illustrated in reaction (9) and (10):

(9)

(10)

For other metal oxides, similar red-ox reactions can be depicted as shown above by balancing the appropriate valences and coefficients for the particular metal oxide selected.

FIGS. 1–4, illustrate that there are no thermodynamic barriers to the conversion of ethane and ethylene to monoethanolamine and ethylenediamine by partial oxidative amination. The non-catalyzed reaction which utilizes oxygen gas as the source of the required oxygen exhibits a highly favorable standard free energy change in all cases. Somewhat less favorable, but still thermodynamically advantageous free energy changes are provided by the use of a suitable metal oxide catalyst or a hydrogenation/dehydrogenation metal catalyst. The chief advantages provided by the use of these catalysts are enhanced selectivity and increased conversion of the hydrocarbon starting materials to monoethanolamine and ethylenediamine. At the same time, the generally lower reaction temperatures at which highly active catalysts operate tend to minimize or eliminate the formation of $NO_x$ by products. For example, FIGS. 1–4 illustrate that a reducible $MnO_2$ catalyst provides a very favorable standard free energy change at a temperature of about 250° K (−23.6° C.) for the partial oxidative amination of both ethylene and ethane to either monoethanolamine or ethylenediamine.

The reaction may be effected by the incremental addition of one of the reactants to the other or by the joint addition of the reactants to the catalyst. The reaction may be carried out by slurrying the catalyst in the reactants (optionally in a solvent) or in a batch or semi-batch mode in an autoclave. Solvents may be used to provide two liquid phases one of which contains the partial oxidative amination catalyst and the other the reactants with a sufficient amount of mixing to effect reaction. A more preferred process effects the reaction in a continuous manner over a fixed bed or fluidized bed of the partial oxidative amination catalyst in a tubular reactor.

Inorganic membrane reactors may be used to control the concentration of reactants (e.g., oxygen) in the partial oxidative amination catalyst bed, and/or to provide a source of the partial oxidative amination catalyst. The reactor may be an inert membrane packed bed reactor (IMPBR), an inert membrane fluidized bed reactor (IMFBR), a catalytic membrane reactor (CMR), a packed bed catalytic membrane reactor (PBCMR), or a fluidized bed catalytic membrane reactor (FBCMR).

In a preferred embodiment, the reaction is carried out in a circulating fluidized bed reactor. Such a reactor is shown schematically in FIG. 5. The reactor, generally designated 100, which includes a riser 102, a separator/stripper 104, a connecting conduit or pipe 106, a regenerator 108 and a stand pipe 110 arranged in a loop around which the solid metal oxide catalyst is continuously circulated. The process carried out by the reactor will be explained in the context of the partial oxidative amination of ethylene to monoethanolamine as illustrated in reaction (4), although it should be understood that essentially the same process has general applicability for the partial oxidative amination of alkanes and/or alkenes to alkanolamines and/or alkyleneamines.

Figure 1A:
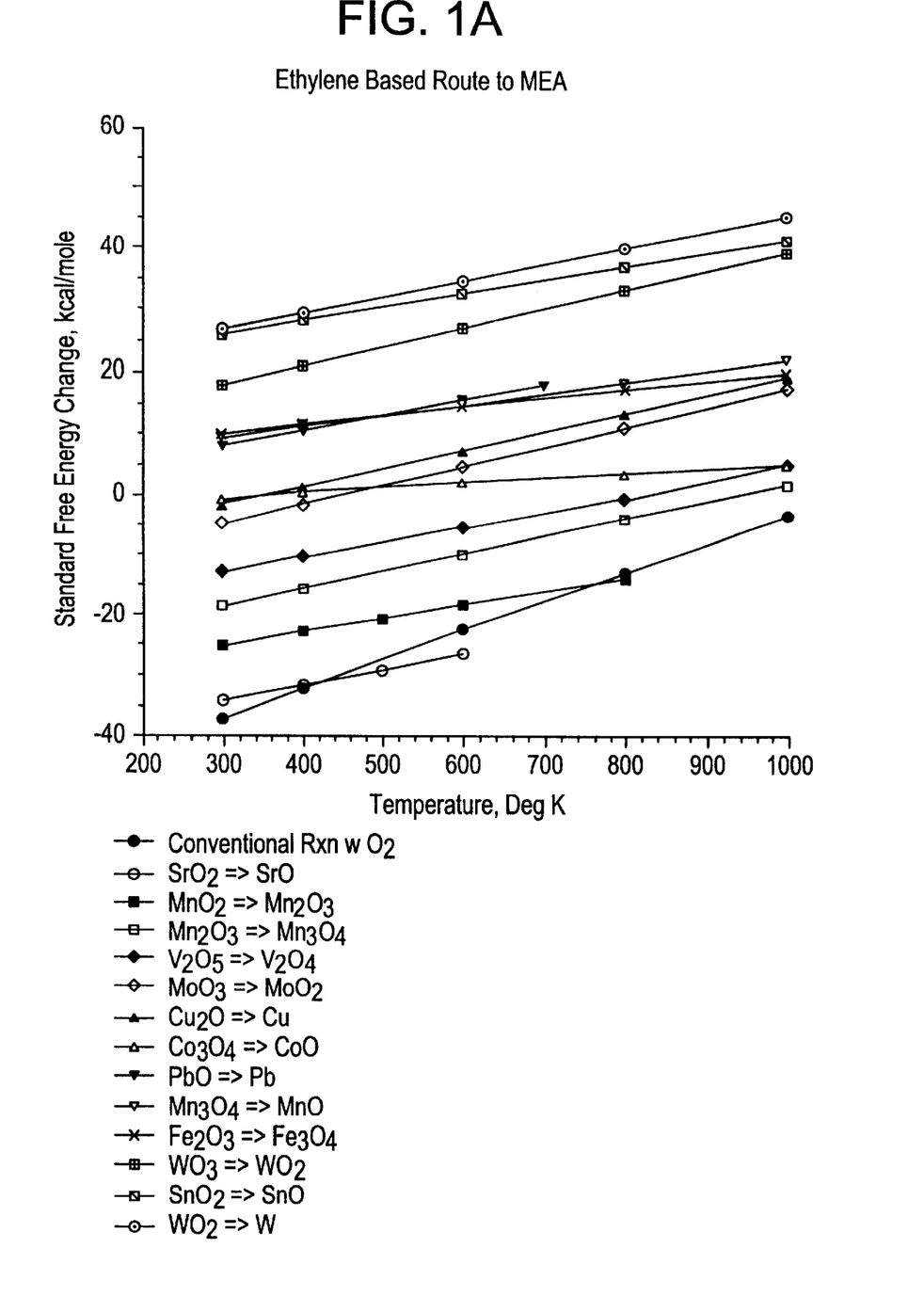
FIG. 1 contains a series of plots illustrating the standard free energy change as a function of temperature for a number of ethylene based routes to monoethanolamine.
Figure 2A:
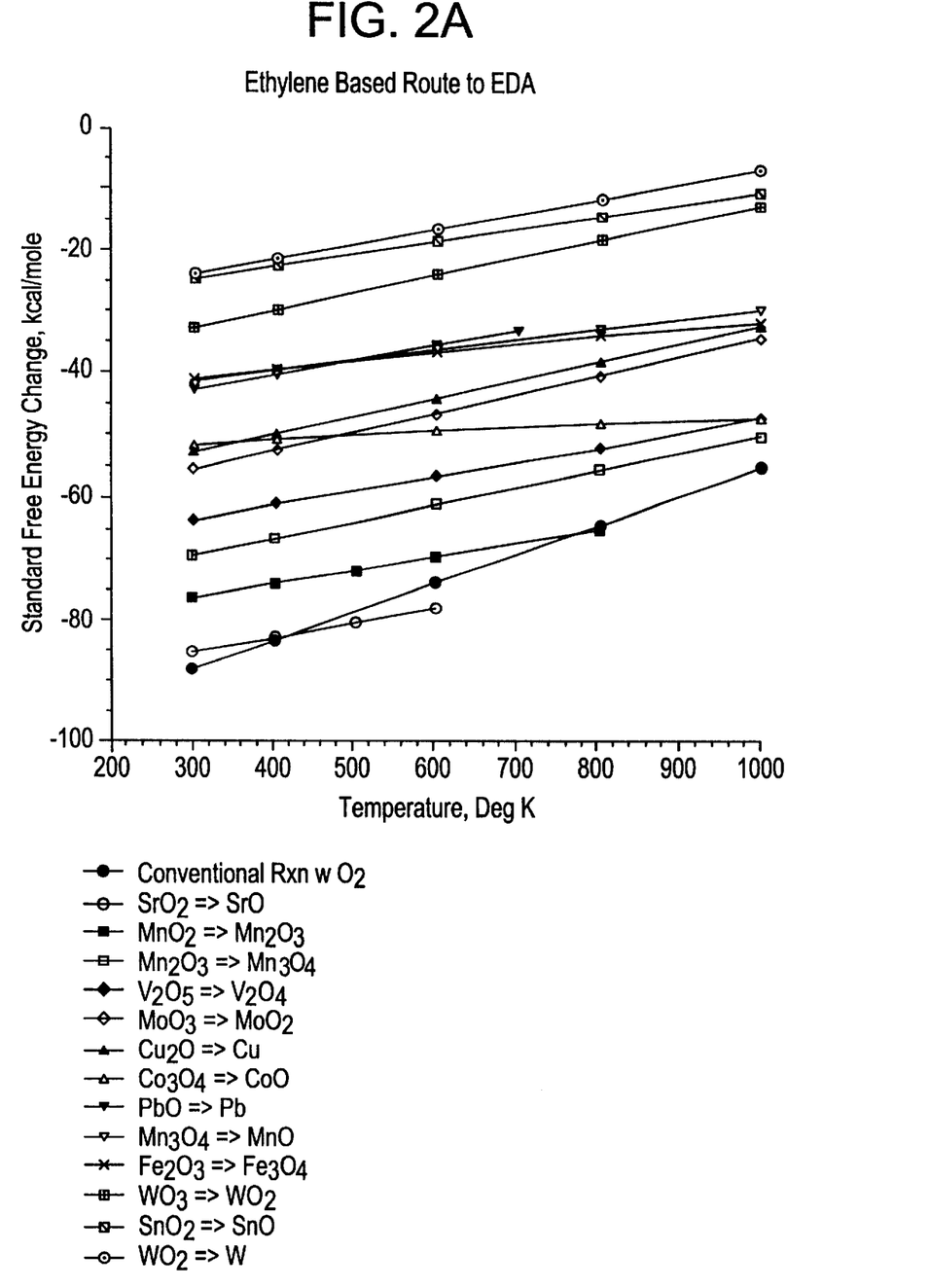
FIG. 2 contains a series of plots illustrating the standard free energy change as a function of temperature for a number of ethane based routes to monoethanolamine.
Figure 3A:
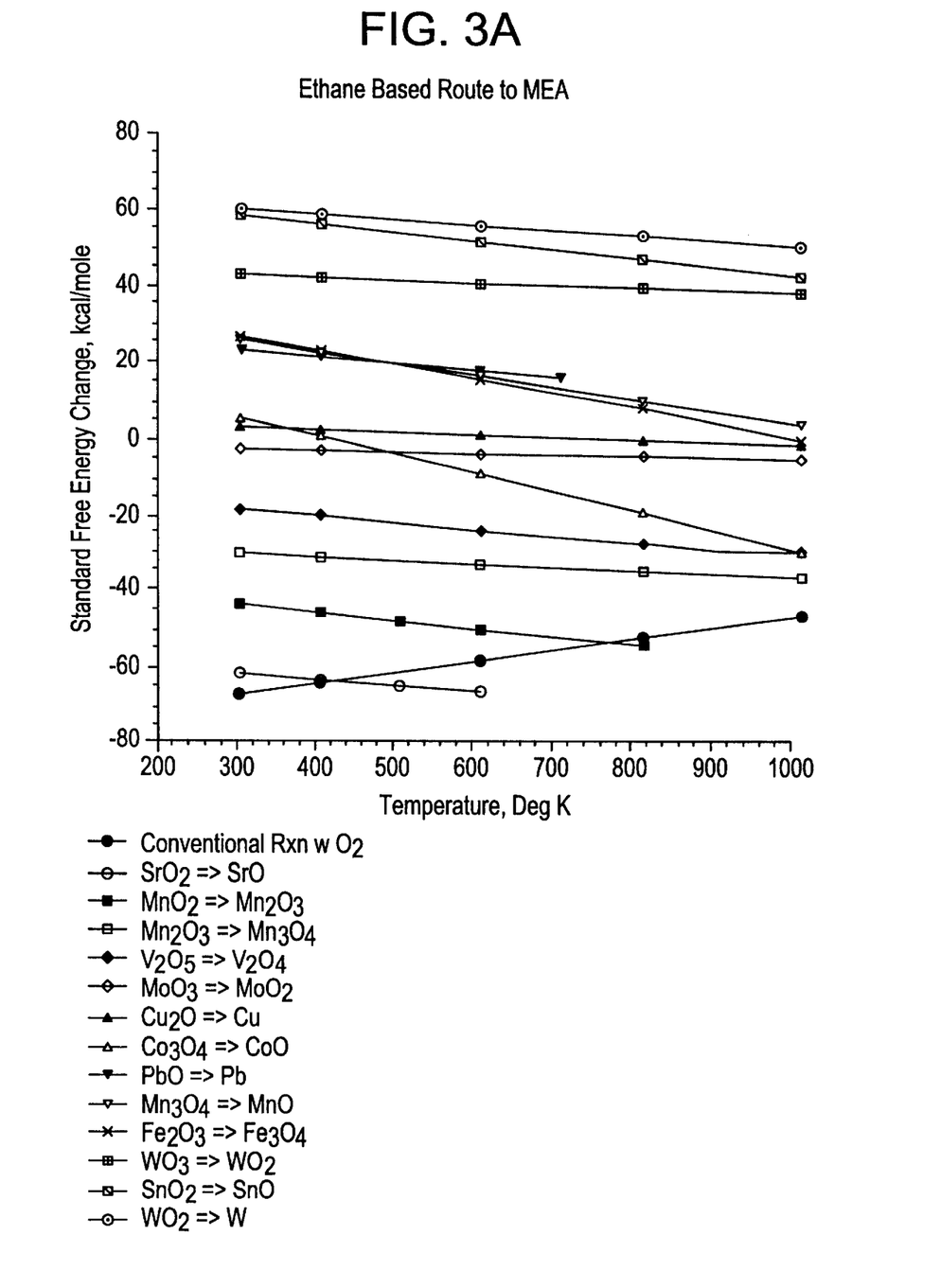
FIG. 3 contains a series of plots illustrating the standard free energy change as a function of temperature for a number of ethylene based routes to ethylenediamine.
Figure 4A:
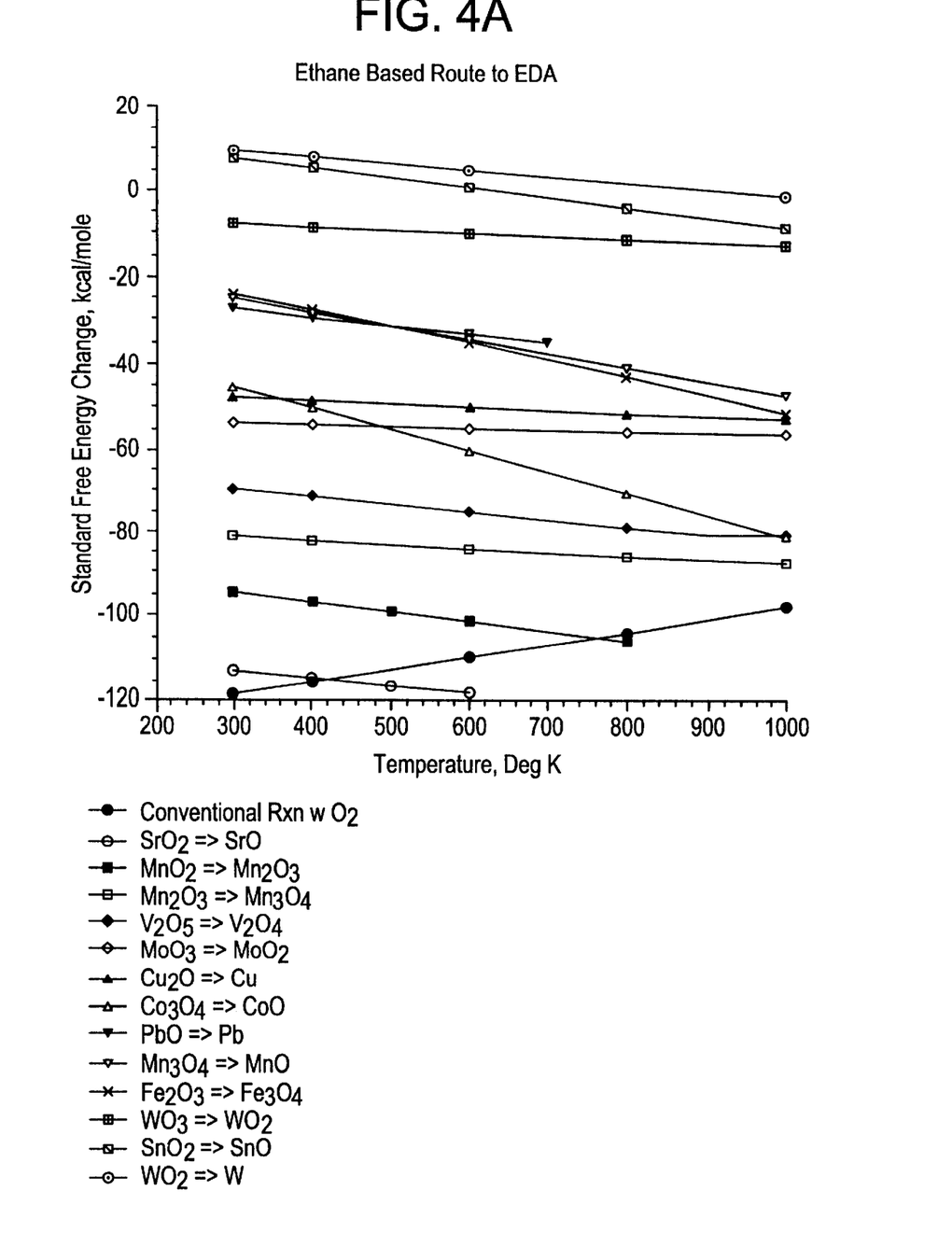
FIG. 4 contains a series of plots illustrating the standard free energy change as a function of temperature for a number of ethane based routes to ethylenediamine.
Figure 5:
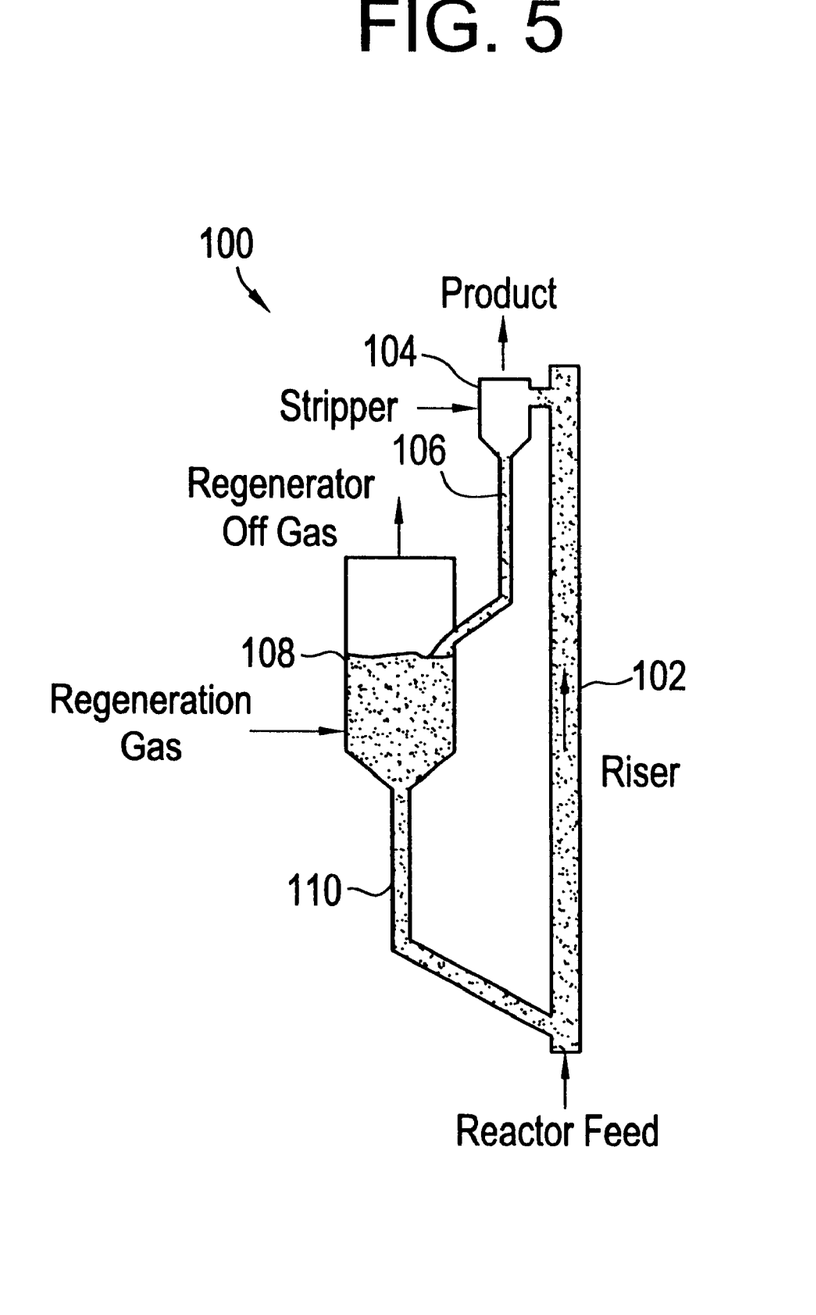
FIG. 5 is schematic illustration of a circulating fluidized bed reactor for carrying out the process of the present invention.

The metal oxide catalyst particles are carried upward in the riser 102 by a stream of high velocity gas containing ethylene and ammonia. The ethylene undergoes partial oxidative amination in the riser and the metal oxide catalyst is converted to its reduced form as illustrated on the right in reactions (4), (5), (9) and (10). The reduced catalyst particles are then separated from the product stream and stripped of any carbonaceous species in the separator/stripper 104 and then passed through the connecting conduit 106 to the regenerator 108. There, the reduced catalyst is reoxidized by exposure to air or some other suitable oxygen-containing gas stream. The reoxidized catalyst is then directed back into the bottom of the riser by the stand pipe 110.

The use of a circulating fluidized bed reactor provides a number of advantages. The essentially plug flow character- istics of gas and catalyst particles in the riser give high selectivity to monoethanolamine, and the absence of oxygen gas in the riser further improves selectivity by reducing monoethanolamine destruction or the undesirable formation of nitrogen oxides. Loosely bound highly active oxygen species are eliminated prior to entry into the riser which results in increased conversion and the maintenance of high catalyst selectivity. The high circulation rate of the catalyst also provides a heat sink which helps control the temperature in the riser and reduces the heat transfer area that would otherwise be required to remove the heat of reaction. Accordingly, the reactor design provides economic as well as process advantages.

While the use of a circulating fluid bed reactor provides important advantages, it should be understood that the invention is not limited in this regard. It should also be understood that regardless of which type of reactor is utilized, should the metal oxide catalyst not provide sufficient oxygen small amounts of additional $O_2$ may be bled into the reaction system. Typically, if additional oxygen is required it is added in an amount less than about 5%, and preferably less than about 2%, based on the total feed.

As noted previously, the present invention has been described in detail in the context of producing monoethanolamine and ethylenediamine by the partial oxidative amination of ethylene and/or ethane. However, those skilled in the art will readily appreciate that the invention has general application for the production of other alkanolamines and alkyleneamines from a variety of alkane and alkene starting materials. For example, propanolamines and diaminopropanes can be formed by the partial oxidative amination of propylene and propane according to essentially the same manner as illustrated in reactions (1)–(9). This is equally true for higher homologs of ethane and ethylene and their associated alkanolamines and alkyleneamines.

Diethanolamine and triethanolamine may also be formed based on the partial oxidative amination of ethane and/or ethylene. In the case of diethanolamine, for example, once monoethanolamine is produced by one or more of the mechanisms illustrated by reactions 1–5, additional ethane and/or ethylene is reacted with monoethanolamine as set forth in reaction (11) to form the desired end product:

(11)

As will be appreciated by those skilled in the art, if additional ethane and/or ethylene is provided, the reaction will proceed to the formation of triethanolamine.

Those skilled in the art will also readily appreciate that the reactions described above are not mutually exclusive. That is, either monoethanolamine or ethylenediamine may be produced, or both of these products may be produced simultaneously. The particular product(s) produced and the particular route(s) by which this is accomplished are determined by controlling the partial pressure of the hydrocarbon raw materials and the partial pressure of the ammonia and the choice of a suitable catalyst.

Accordingly, the present invention provides a practicable and economic means of producing a wide variety of alkanolamines and alkyleneamines based on the use of alkanes and/or alkenes as the hydrocarbon starting materials.

Although specific embodiments illustrating the invention have been disclosed, it should be understood that the invention has been described by way of example and not by limitation.

What is claimed is:

1. A process for synthesizing at least one of an alkanolamine and an alkyleneamine, said process including the step of:

reacting an alkane and/or an alkene with a source of oxygen, a source of nitrogen including at least one of ammonia, hydrazine, amines, and nitrous oxide in the presence of a reducing gas and, optionally, additional hydrogen to convert said alkane and/or alkene by partial oxidative amination to at least one of said alkanolamine and alkyleneamine.

2. The process of claim 1, wherein the source of nitrogen is at least one of ammonia, hydrazine, amines, and nitrous oxide in the presence of a reducing gas.

3. The process of claim 1, wherein the source of oxygen is at least one of oxygen, ozone, oxides of nitrogen, water, and alcohols.

4. The process of claim 1, wherein the oxygen is provided by at least one metal oxide catalyst.

5. The process of claim 4, wherein the metal oxide catalyst comprises at least one metal oxide that is reduced by reaction with a hydrocarbon moiety to a lower oxidation state such that the metal oxide provides a lower standard free energy for the partial oxidative amination of the alkane and/or alkene.

6. The process of claim 4, wherein the catalyst is regenerable.

7. The process of claim 4, wherein the alkane and/or alkene is reacted with the source of nitrogen over the catalyst in a circulating fluidized bed reactor.

8. The process of claim 6, wherein the metal oxide catalyst is regenerated by exposing the catalyst to a source of oxygen.

9. The process of claim 1, wherein ethane and/or ethylene is reacted with ammonia and oxygen to form at least one of monoethanolamine and ethylenediamine.

10. The process of claim 1, wherein the ammonia is provided at a partial pressure which determines the ratio of alkanolamine and alkyleneamine synthesized.

11. The process of claim 1, wherein in addition to a source of nitrogen and a source of oxygen the alkane and/or alkene is reacted with a source of hydrogen.

12. The process of claim 11, wherein a hydrogenation/dehydrogenation catalyst is present with the source of hydrogen.

13. The process of claim 1, wherein the reaction is carried out in one of gas, liquid, multi-phase, and super critical media.

14. The process of claim 9, wherein the alkanolamine is monoethanolamine which is reacted further to form at least one of diethanolamine and triethanolamine.

15. A process for synthesizing at least one of an alkanolamine and an alkyleneamine, said process including the step of:

reacting an alkane and/or an alkene with a source of oxygen, a source of nitrogen and, optionally, additional hydrogen to convert said alkane and/or alkene by partial oxidative amination to at least one of said alkanolamine and alkyleneamine.

* * * * *